(12) United States Patent
Weil et al.

(10) Patent No.: US 6,419,899 B1
(45) Date of Patent: Jul. 16, 2002

(54) SUSPENSION AEROSOL FORMULATIONS OF PHARMACEUTICAL PRODUCTS

(75) Inventors: Hans-Hermann Weil, Gau-Bickelheim; Ottfried Daab, Ingelheim, both of (DE)

(73) Assignee: Boehringer Ingelheim KG, Ingelheim (DE)

( * ) Notice: Subject to any disclaimer, the term of this patent is extended or adjusted under 35 U.S.C. 154(b) by 0 days.

(21) Appl. No.: 09/525,431

(22) Filed: Mar. 14, 2000

Related U.S. Application Data

(63) Continuation of application No. 09/990,252, filed on Dec. 15, 1997, now abandoned, which is a continuation of application No. 08/597,230, filed on Feb. 6, 1996, now abandoned, which is a continuation of application No. 08/282,402, filed on Jul. 28, 1994, now abandoned, which is a continuation of application No. 07/910,353, filed on Oct. 1, 1992, now abandoned.

(30) Foreign Application Priority Data

Jan. 31, 1990 (WO) ............................... PCT/EP91/00178
Feb. 3, 1990 (DE) ....................................... P 40 03 270

(51) Int. Cl.⁷ .................................................. A61K 9/12
(52) U.S. Cl. ............................ 424/45; 424/46; 424/489
(58) Field of Search ............................ 424/45, 46, 489

(56) References Cited

U.S. PATENT DOCUMENTS

| | | | | |
|---|---|---|---|---|
| 4,174,295 A | * | 11/1979 | Bargigia et al. | |
| 4,352,789 A | | 10/1982 | Thiel | |
| 4,814,161 A | | 3/1989 | Jinks et al. | |
| 5,118,494 A | * | 6/1992 | Schultz et al. | |
| 5,182,097 A | * | 1/1993 | Byron et al. | |
| 5,605,674 A | * | 2/1997 | Purewal et al. | |
| 6,153,173 A | * | 11/2000 | Sapsford et al. | |

FOREIGN PATENT DOCUMENTS

| | | | |
|---|---|---|---|
| CA | 2075058 | * | 8/1991 |
| EP | 0 247 608 | | 12/1987 |
| EP | 0 384 371 | | 8/1990 |
| GB | 902590 | | 8/1961 |
| JP | 55 131 096 | | 12/1980 |
| WO | 86/04233 | | 7/1986 |

OTHER PUBLICATIONS

Deger et al., "Specialty fluoroaliphatic chemicals"; a paper presented by Chemspec USA 1989; a symposium highlighting innovation, manufacture and applications of specialty chemicals, held at Hyatt Regency Chicago Hotel, 10–11 Oct. 1989.

Hoechst Press Release #7252; "Hoechst: Development of Alternatives to Fully Halogenated CFC's Takes Priority"; 1989.

Fischer et al., "CFC Propellant Substitution: International Perspectives"; Pharm. Technol., Inc., 1989; 1(2), 16–18.

Lachman et al., The Theory of Practice of Industrial Pharmacy"; 1986, Philadelphia, Ch. 20 p. 590 and 603–604.

* cited by examiner

*Primary Examiner*—Raj Bawa
(74) *Attorney, Agent, or Firm*—Robert P. Raymond; Mary-Ellen M. Devlin; Alan R. Stempel

(57) ABSTRACT

Pharmaceutical preparations for producing powder aerosols using propellant gases which use TG 227, and possibly also TG 11, TG 12, TGH 114, propane, butane, pentane or DME.

5 Claims, No Drawings

SUSPENSION AEROSOL FORMULATIONS OF PHARMACEUTICAL PRODUCTS

This application is a continuation of U.S. Ser. No. 08/990,252, filed Dec. 15, 1997, now abandoned, which is a continuation of U.S. Ser. No. 08/597,230, filed Feb. 6, 1996, now abandoned, which is a continuation of U.S. Ser. No. 08/282,402, filed Jul. 28, 1994, now abandoned, which is a continuation of U.S. Ser. No. 07/910,353, filed Oct. 1, 1992, now abandoned.

BACKGROUND OF THE INVENTION

The invention relates to new propellant gases which contain as a typical ingredient 1,1,1,2,3,3,3-heptafluoropropane (TG 227), the use of these propellant gases in pharmaceutical preparations suitable for producing aerosols, and these pharmaceutical preparations themselves.

Aerosols of powdered (micronised) drugs are used widely in therapy, e.g., in the treatment of obstructive diseases of the respiratory tract. If such aerosols are not produced by atomizing the pharmaceutical powder or by spraying solutions, suspensions of the drugs in liquefied propellant gases are used. The latter consist primarily of mixtures of TG 11 (trichlorofluoromethane), TG 12 (dichlorodifluoromethane) and TG 114 (1,2-dichloro-1,1,2,2-tetrafluoroethane), optionally with the addition of lower alkanes such as butane or pentane, or with the addition of DME (dimethylether). Mixtures of this kind are known for example from German Patent 1178975.

Owing to their harmful effect on the earth's atmosphere (destruction of the ozone layer, Greenhouse effect) the use of chlorofluorocarbons has become a problem, with the result that the search is on for other propellant gases or propellant gas mixtures which do not have the above-mentioned harmful effects or, at least, have them to a lesser degree.

However, this search has come up against major problems, since propellant gases for therapeutical use have to satisfy numerous criteria which cannot easily be reconciled, e.g., in terms of toxicity, stability, vapor pressure, density and solubility characteristics.

THE INVENTION

As has now been found, TG 227 (1,1,1,2,3,3,3-heptafluoroporpane, optionally in admixture with one or more propellant gases from the group comprising TG 11 (trichlorofluoromethane), TG 12 (dichlorodifluoromethane), TG 114 (1,2-dichloro-1,1,2,2,-tetrafluoroethane), propane, butane, pentane and. DME.

(tert.-butylamino)ethanol.

Examples of Anticholinergics:

Ipratropium bromide

Oxitropium bromide

Trospium chloride

Benzilic acid-N-P-fluoroethylnortropine ester methobromide

Examples of Steroids:

Budesonide

Beclomethasone (or the 17, 21-dipropionate thereof)

Dexamethason-21-isonicotinate

Flunisolide

Examples of Anti-allergics:

Disodium cromoglycate

Nedocromil

Examples of PAF-antagonists:

4-(2-Chlorophenyl)-9-methyl-2-[3-(4-morpholinyl)-3-propanon-1-yl]-6H-thieno [3.2-f][1.2.4]triazolo[4.3-a][1.4]diazepine.

3-(Morpholin-4-yl-carbonyl)-5-(2-chlorphenyl)-10-methyl-7H-cyclopental[4.5]thieno-[3.2-f][1.2.4]triazolo[4.3-a][1.4]diazepine 3-(Di-n-propylamincarbonyl)-5-(2-chlorphenyl)-10-methyl-7H-cyclopental[4.5]thieno-[3.2-f][1.2.4]triazolo[4.3-a][1.4]diazepine The active substances may also be combined, e.g., betamimetics plus anticholinergics or betamimetics plus anti-allergics.

Examples of Preparations According to the Invention (Amounts Given in Percent by Weight):

1) 0.10% Oxitropium bromide 0.01% Soya lecithin 4.0% Pentane 95.89% TG 227

2) 0.3% Fenoterol 0.1% Soyalecithin 10.0% Pentane 70.0% TG 227

19.6% TG 134a

What is claimed is:

1. A suspension aerosol pharmaceutical formulation for administration of micronised or powdered drug to the respiratory tract of a warm-blooded animal via inhalation comprising 1,1,1,2,3,3,3-heptafluoropropane and one or more additional propellant gases selected from the group consisting of trichlorofluoromethane, dichlorodifluoromethane, 1,2-dichloro-1,1,2,2-tetrafluoroethane, propane, butane, pentane and dimethylether.

2. The pharmaceutical formulation as recited in claim 1 wherein the micronised drug is selected from the group consisting of clenbuterol, salbutamol, salmeterol and terbutalin.

3. The pharmaceutical formulation as recited in claim 1 wherein the micronised drug is selected from the group consisting of ipratropium bromide and oxitropium bromide.

4. The pharmaceutical formulation as recited in claim 1 wherein the micronised drug is selected from the group consisting of budesonide, beclomethasone and flunisolide.

5. The pharmaceutical formulation as recited in claim 1 wherein the micronised drug is disodium cromoglycate or nedocromil.

* * * * *